United States Patent [19]

Watts, Jr.

[11] 4,022,830
[45] May 10, 1977

[54] PROCESS FOR PREPARING POLYCHLOROBENZAMIDE DERIVATIVES

[75] Inventor: Lewis W. Watts, Jr., Austin, Tex.

[73] Assignee: Texaco Development Corporation, New York, N.Y.

[22] Filed: Aug. 15, 1975

[21] Appl. No.: 605,113

Related U.S. Application Data

[63] Continuation-in-part of Ser. No. 379,545, July 16, 1973, abandoned.

[52] U.S. Cl. .............................. 260/559 R; 71/118; 424/324; 260/45.9 NC; 260/558 D; 260/559 S
[51] Int. Cl.² ...................................... C07C 102/08
[58] Field of Search ............... 260/558, 559, 559 R, 260/559 S

[56] References Cited

UNITED STATES PATENTS

| | | | |
|---|---|---|---|
| 3,401,191 | 9/1968 | Belf | 260/465 |
| 3,444,196 | 5/1969 | Schoot | 260/558 |

OTHER PUBLICATIONS

Sudborough et al., S. Chem. Soc. (London), vol. 71, pp. 229–234 (1897).
Sudborough, S. Chem. Soc. (London), vol. 67, pp. 601–604 (1895).
Montagne, Rec. Trav. Chim. vol. 21, pp. 385–386 (1902).
Reich, Bull. Chem. Soc. France, vol. 21, pp. 217–223 (1917).
Griffiths et al., Biochem. J., vol. 98, pp. 770–771 (1966).
Birchall et al., J. Chem. Soc., Part C, 1971, pp. 1343–1348.

*Primary Examiner*—John D. Randolph
*Attorney, Agent, or Firm*—Carl G. Ries; Thomas H. Whaley; Lee G. Meyer

[57] ABSTRACT

A novel process for preparing polychlorobenzamide derivatives, useful as biocidal agents, flame retardants in plastic resins, and the like, from corresponding polychlorobenzonitrile compound in near quantitative yields is disclosed. A polychlorobenzonitrile compound is admixed and reacted with excess sulfuric acid at an elevated temperature e.g. 100° to 160° C for a time period sufficient to hydrolyze the polychlorobenzonitrile derivative to the corresponding polychlorobenzamide derivative. The reaction product is then recovered to provide the corresponding polychlorobenzamide derivative in an excellent yield above about 90%.

5 Claims, No Drawings

PROCESS FOR PREPARING POLYCHLOROBENZAMIDE DERIVATIVES

CROSS REFERENCE TO RELATED APPLICATIONS

This application is a continuation-in-part of application Ser. No. 379,545 filed July 16, 1973, now abandoned.

BACKGROUND OF THE INVENTION

This invention relates to an improved process for preparing polychlorobenzamide derivatives and more particularly pertains to a process for synthesizing said derivatives from corresponding polychlorobenzonitrile compound in near quantitative yields.

Polyhalobenzamide derivatives are well known compounds that are highly effective biocidal agents, e.g., fungicides, herbicides, bactericides, and the like. Furthermore, the derivatives are useful as progenitors of secondary and tertiary amides, (e.g. N-alkyl, N,N-dialkyl, N-aryl, N,N-diaryl) that are known biocidal agents. The compounds may also be used in flame-retardant resins, plasticizers, dyes, coatings and the like.

However, the utilization of polyhalobenzamide derivatives has been somewhat restricted in view of the limited production and expense of the compounds. Apparently this has been due to several factors, e.g., the relative inaccessability of suitable precursors and low yields of the derivatives prepared by prior art processes.

There are a few processes known in the art for the preparation or synthesis of certain polyhalobenzamide derivatives. For example, British Pat. No. 1,085,474 (1967) discloses a process for producing pentachlorobenzamide and four other derivatives by treating pentachlorobenzoyl chloride with appropriate co-reactants. However, the preparation of polyhalobenzamide derivatives by this process is disadvantageous in that polyhalobenzoyl chloride derivatives are not available in economical commercial quantities. Hence, the preparation of polyhalobenzamide derivatives in accordance with the teachings of this process would appear to be quite expensive, from a commercial standpoint.

Another prior art process is disclosed in U.S. Pat. No. 3,313,859 to Dorfman et al. (1967). Dorfman et al. teach a process for producing tetrahalohydroxybenzamides wherein a pentahalobenzamide is heated with a strong base dissolved in a solvent quantity of ethylene glycol or methanol. It is believed readily apparent that the process disclosed by Dorfman et al. has the disadvantage of starting with a polyhalobenzamide derivative as a precursor. As stated hereinbefore, polyhalobenzamide derivatives including pentahalobenazmides, prepared by prior art processes are quite expensive and are in relatively short supply, from a commercial standpoint.

On the other hand, processes for producing polyhalobenzonitrile derivatives in relatively economical commercial amounts have recently been developed. Commercial quantities of certain polyhalobenzonitrile derivatives, e.g., pentachlorobenzonitrile, are readily available.

There are classical methods known in the art to effect the conversion of nitrile derivatives to amide derivatives, for example, mixing and reacting a nitrile with hot caustic, hot alcoholic caustic, mixtures of phosphoric and acetic acids, and the like. However, experiments have shown that the classical methods fail to effect the conversion of polyhalobenzonitrile derivatives to corresponding polyhalobenzamide derivatives particularly in yields that are economically feasible, e.g., yields greater than 90%.

It has been previously reported that various aromatic nitriles are hydrolyzed to the corresponding acid by boiling the nitrile for several hours with 60 to 70% sulfuric acid. However, some aromatic nitriles in which substitution occurs in the two ortho positions have been shown to produce only the amide. Claus and Storenhagen (Ann. 1892, 269,228) report that 2:6 dichlorobenzonitrile is the notable exception being converted directly to the corresponding acid when heated at 150° C.

It is well known that in hydrolyzing nitriles, an amide intermediate is formed; however, in most cases the amide is further hydrolyzed to the acid. For example, Sodbrough, Jackson and Lloyd, at page 232 disclose that 2:4:6-trichlorobenzamide is hydrolyzed at 160° C in the presence of excess 75% sulfuric acid to the corresponding acid with a 48.18 wt. % conversion.

Unexpectedly and contrary to the teachings of the prior art, it has now been discovered that a polychlorobenzonitrile compound having at least four chloro substituents can be directly converted to the corresponding polychlorobenzamide with essentially no further hydrolysis to the acid in accordance with the instant invention.

SUMMARY OF THE INVENTION

In accordance with the instant invention we have found that polychlorobenzamide derivatives of the formula:

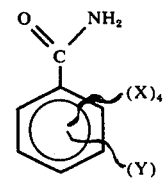

wherein X is a chloro radical and Y is a chloro radical or a hydroxy radical can be synthesized in near quantitative yields by mixing and reacting a corresponding polychlorobenzonitrile of the formula:

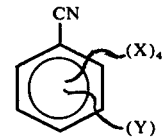

wherein X is a chloro radical and Y is a chloro radical or a hydroxy radical with sulfuric acid at elevated temperatures for a time period sufficient to effect the hydrolysis of the polychlorobenzamide derivative and recovering the resultant product. The inventive method provides a resultant polychlorobenzamide derivative of high purity in almost quantitative yields, i.e., above about 90%. The process is especially useful for the preparation of pentachlorobenzamide from corresponding pentachlorobenzonitrile which has recently become available in economical commercial quantities, as mentioned hereinbefore.

DESCRIPTION OF THE PREFERRED EMBODIMENTS

In carrying out the instant invention, a polychlorobenzonitrile derivative, of the formula disclosed hereinabove, is admixed and reacted with an excess of sulfuric acid at an elevated temperature of between about 90° to 170° C for a time period sufficient to hydrolyze the polyhalobenzonitrile compound to the corresponding polyhalobenzamide derivative. The reaction product is then isolated and recovered. This procedure gives rise to the corresponding polychlorobenzamide derivative in excellent yield, i.e., above 90%.

It is essential in the practice of the invention to mix and react the polyhalobenzonitrile derivative with sulfuric acid of sufficient concentration to effect hydrolysis. Unexpectedly it has been found that sulfuric acid concentrations below about 50 wt. % do not effect the hydrolysis and only starting product is obtained. Sulfuric acid concentrations in the range of 75% $H_2SO_4$ by total weight or greater are preferred. Preferrably, excess of the above-described concentrated sulfuric acid is utilized in concentrations and/or amounts sufficient to provide a molar excess of acid in the reaction mixture.

The acid hydrolysis of the polychlorobenzonitrile derivative is preferably accomplished by adding the sulfuric acid in molar excess to the derivative and then heating the mixture to between about 100° to 170° C. Alternatively, the concentrated sulfuric acid may be heated, added to the polyhalobenzonitrile derivative and the resulting mixture then heated to the desired reaction temperature.

Experiments have shown that sulfuric acid hydrolysis of polychlorobenzonitrile derivatives at temperatures within the above-described range produces the corresponding polychlorobenzamide derivatives in near quantitative yields, e.g., greater than 90% yield. On the other hand, acid hydrolysis at a temperature below about 80° C produces low yields of the corresponding polychlorobenzamides, even when held for extended periods of time. Accordingly, heating the polychlorobenzonitrilesulfuric acid reaction mixture at temperatures above about 180° C produces low yields of the corresponding polyhalobenzamide along with no appreciable amounts of the corresponding polyhalobenzoic acid derivative. Temperatures in excess of 180° C result in decomposition of the starting material. The optimum temperature utilized during acid hydrolysis is primarily dependent upon the particular polychlorobenzonitrile derivative utilized. For example, when synthesizing pentachlorobenzamide, it is preferred to utilize a temperature within the range of about 130° to 160° C. Accordingly, when preparing hydroxytetrachlorobenzamide, the optimum temperature is about 100° to 150° C.

The excess sulfuric acid is mixed and reacted with the polychlorobenzonitrile within the above-described elevated temperature range for a time period that is sufficient to hydrolyze the polychlorobenzonitrile derivative to the corresponding polyhalobenzamide derivative in a yield approaching 100%. The reaction time is primarily dependent upon the type of benzonitrile derivative being hydrolyzed and the range of temperatures utilized. Of course, it will be readily understood that the time period required to effect the hydrolysis is inverse to the temperature utilized, i.e., the higher the temperature the shorter the time period required within the above-described temperature ranges.

The minimum reaction time is that which will effect a complete dissolution of the specific benzonitrile derivative being hydrolyzed at the specific temperature employed. Accordingly, the maximum reaction time is that which will produce a maximum yield of the corresponding polychlorobenzamide derivative at the desired temperature utilized. Preferably, excess sulfuric acid is mixed and reacted with the polychlorobenzonitrile derivative at the above-described elevated temperature range for between about ¼ to 1½ hours. Tests have shown that these reaction times at the preferred temperatures provide resultant corresponding benzamide derivatives in excellent yields (above about 90%).

After the acid reaction step, the reaction product is isolated and recovered to provide the corresponding polychlorobenzamide derivative by any conventional means known in the art. Preferably, the reaction product is isolated by pouring the reaction mixture over cracked ice which causes substantially immediate precipitation of the solid polychlorobenzamide derivative. The solid polychlorobenzamide derivative can then be recovered by any conventional means, such as by filtration, centrifugation and the like.

The present inventive process is particularly effective for the preparation of pentachlorobenzamide in excellent yields (above about 90%) from pentachlorobenzonitrile. As mentioned hereinbefore, pentachlorobenzonitrile has recently become readily available in commercial quantities and at attractive prices. Hence, through the practice of the instant invention, pentachlorobenzamide may also be produced at attractive prices for use as a biocidal agent, in flame retardant resins and as a precursor for other compounds.

In a preferred embodiment of the invention, pentachlorobenzonitrile is interacted with a molar excess of sulfuric acid having at least 75% by weight $H_2SO_4$ at a temperature of between about 130° and 160° C for about 15 to 90 minutes. The reaction mixture is then cooled and diluted with water to form a solid pentachlorobenzamide precipitate. The resultant pentachlorobenzamide is recovered in yields on the average of above about 90%.

In another preferred embodiment of the instant invention, hydroxytetrachlorobenzamide is produced from pentachlorobenzonitrile in a substantially two-step process. Firstly, the compound pentachlorobenzonitrile is mixed and reacted with a compound selected from the group consisting of alkali metal or alkaline earth hydroxides and alkali metal or alkaline earth salts of lower alkyl monocarboxylic acids having up to about 5 carbon atoms per molecule, at an elevated temperature of about 100° to about 150° C in the presence of a suitable solvent, e.g., dimethylsulfoxide, dimethylformamide and the like, which results in the production of hydroxytetrachlorobenzonitride. This resultant product is then mixed and reacted with a molar excess of sulfuric acid having 75% by weight $H_2SO_4$ at an elevated temperature of about 100° to 150° C for about 15 to 60 minutes to provide the resultant reaction product, hydroxytetrachlorobenzamide, recoverable in a yield above about 90% on the average.

Examples of preferred compounds employed in accordance with the above-described embodiment for firstly preparing the hydroxytetrachlorobenzonitrile include sodium hydroxide, potassium hydroxide and sodium and potassium acetates, propionates and the like. Experiments have shown that when these compounds are utilized hydroxytetrachlorobenzonitrile can be recovered in almost quantitative yields.

The following examples are given for the purpose of illustration, and not by way of limitation.

EXAMPLE I

A mixture of 18.0 gms. pentachlorobenzonitrile and 200 ml concentrated sulfuric acid (97 weight % $H_2SO_4$) was heated to 145° C over a period of approximately 40 min. Complete dissolution of the pentachlorobenzonitrile was observed to occur at 130° C thereby giving a pale straw solution. When cool, the reaction mixture was poured onto ice and the white solid thereby formed was isolated by filtration. In this manner there was formed 18.0 gms. (94% yield) pentachlorobenzamide. Identity of the product was established with the aid of both analytical and spectral data.

Analysis: Calculated for $C_7H_2Cl_5NO$; 28.66%, C; 0.69%, H; 60.42%, Cl; and 4.77%, N. Found; 59.3%, Cl; 4.60%, N.

EXAMPLE II

Treatment of 90.0 gms. pentachlorobenzonitrile with 600 ml concentrated sulfuric acid at 150° C for 1 hour gave a straw solution which, when cool, was poured onto ice. Filtration gave rise to 92 gms. (96% yield) pentachlorobenzamide; crystallization from ethanol resulted in the formation of colorless plates, m.p. 268°–270° C.

Analysis: Found, 4.18% N.

EXAMPLE III

Only starting material was recovered when a mixture of pentachlorobenzonitrile (20.0 gms.), phosphoric acid (100 ml), and acetic acid (100 ml) was refluxed for 5 hours.

Example IV

Pentachlorobenzonitrile (12.7 gms.) was isolated upon treatment of 13.7 gms. pentachlorobenzonitrile with 180 ml of 30% caustic for 10 hours.

EXAMPLE V

Into a 500 cc three neck flask was placed 7.0 grams pentachlorobenzonitrile, 12.0 grams sodium acetate, and 200 cc dimethylsulfoxide. The resulting mixture was stirred under nitrogen for 4 hours at 130° C then poured into 1500 cc water. Acidification of the aqueous solution with concentrated hydrochloric acid resulted in the appearance of a white solid material that was isolated by filtration. This solid was allowed to dissolve in ether and the resulting etheral solution treated with magnesium sulfate. After removal of the solvent under reduced pressure there remained 6.0 grams of white crystalline solid that was subsequently shown to be hydroxy-tetrachlorobenzonitrile; 97.6% yield.

EXAMPLE VI

A mixture of 25.9 grams of hydroxy-tetrachlorobenzonitrile, prepared in accordance with Example V, and 150 ml concentrated sulfuric acid was heated under an inert atmosphere at 130° C for 15 minutes. Pouring the cool reaction mixture on crushed ice produced a white solid which, when filtered and dried weighed 26.8 grams. This material was subsequently shown to be hydroxy-tetrachlorobenzamide.

EXAMPLE VII

A mixture of 20.0 g (0.036 moles) pentachlorobenzonitrile, 10.0 g potassium hydroxide, and 400 cc dimethylsulfoxide was heated at 120° C for 4 hours. When cool, the crude reaction mixture was diluted with $H_2O$, then filtered. The resultant product, hydroxy-tetrachlorobenzonitrile weighed 16.16 g (100% yield) and exhibited a melting point of 214°–215.5° C (needles from tetrahydrofuran).

Elemental Analysis: Calculated for $C_7HCl_4NO$ (molecular weight 256.89); 32.72%, C; 0.39%, H; 55.20%, Cl; 5.23%, N; 6.23%, O. Found: 32.64%, C; 0.45%, H; 55.49%, Cl; 5.46%, N.

Spectral Analysis:
Mass: Parent molecular ion, 255 m/e.
NMR: Singlet, 5.52τ
IR: 3.0μ (—OH); 4.45μ (—CN).

A 10.0 g portion of this hydroxy-tetrachlorobenzonitrile was heated under an inert atmosphere at 130° C for 15 minutes with 150 ml concentrated sulfuric acid. The product, hydroxytetrachlorobenzamide was readily isolated by filtering the $H_2O$-diluted reaction mixture; yield 97.0%.

Elemental Analysis: Calculated for $C_7H_3Cl_4NO_2$; 30.79%, C; 0.37%, H; 51.94%, Cl; 5.13%, N. Found; 31.98%, C; 1.34%, H; 50.69%, Cl.

EXAMPLE VIII

An attempt to convert pentachlorobenzonitrile into pentachlorobenzamide in the presence of sodium hydroxide and ethylene glycol (reflux, 10 hours) in accordance with the process disclosed in Example I gave little, if any amide or ester.

EXAMPLE IX

To a clean, dry 500 cc flask fitted with a reflux condenser, thermometer and magnetic stirrer was added 75.5 gms. (0.1 moles) pentachlorobenzonitrile and 300 ml sulfuric acid having 50% by weight $H_2SO_4$ content. The mixture was then heated to reflux temperature of about 120° C and refluxed continuously for 24 hours. The reaction mixture was poured onto cracked ice and the resultant cooled admixture filtered. A light tan solid residue weighing 30 grams was recovered and air dried for approximately 4 hours. Analysis of the residue by infrared spectroscopy showed only starting material, i.e., pentachlorobenzonitrile with no evidence of the presence of the acid or the amide.

EXAMPLE X

In this example, 27.5 grams (0.1 mole) pentachlorobenzonitrile and 300 ml of 70% $H_2SO_4$ was charged into a clean, dry 500 ml glass flask fitted with reflux condenser, thermometer, and magnetic stirrer. The reaction mixture was heated to 170° C with stirring and held at this temperature for 7½ hours. The resultant crude reaction product mixture was then admixed with an excess of a mixture of ice and water. The cooled admixture was filtered and a pale tan solid residue weighing 31 grams was collected. Upon analysis by infrared spectroscopy the residue was shown to contain about 95% by weight pentachlorobenzamide. An unknown having an absorption band at about 5.95μ accounted for about 5% of the residue material. This unknown material falls in the known absorption region for aromatic carboxylic acids but no pentachlorobenzoic acid could be specifically identified.

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A process for preparing a polychlorobenzamide derivative with essentially no further hydrolysis to the acid in commercially economical yields from the corresponding polychlorobenzonitrile compound having the formula:

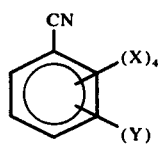

wherein X is selected from a group consisting of a chloro radical and Y is a hydroxy radical comprising the step of:
   initially admixing and reacting said polychlorobenzonitrile compound with a molar excess of sulfuric acid of a concentration sufficient to hydrolyze said polychlorobenzonitrile compound at elevated temperatures of from about 100° to 170° C to form a reaction mixture containing said polychlorobenzamide derivative.

2. The process of claim 1 comprising the further step of:
   isolating said formed polychlorobenzamide derivative by diluting and cooling the reaction mixture with water such that said polyhalobenzamide derivative precipitates as a solid and separating said solid by filtration.

3. The process of claim 1 wherein said polychlorobenzonitrile is 4-hydroxytetrachlorobenzonitrile; wherein said concentrated sulfuric acid has a concentration in excess of 94% $H_2SO_4$ by total weight and wherein said elevated temperature is about 135° to 145° C.

4. The process of claim 1 wherein said concentration of sulfuric acid is greater than about 70% by total weight.

5. A process for preparing hydrotetrachlorobenzamide derivative with essentially no further hydrolysis to the acid in commercially economical yields from the corresponding hydroxychlorobenzonitrile compound comprising the step of
   admixing and reacting said hydrotetrachlorobenzonitrile compound with a molar excess of sulfuric acid at a concentration of about 75% and at elevated temperatures of 150°–170° C.

* * * * *